United States Patent [19]

Nakanishi

[11] Patent Number: 4,493,645
[45] Date of Patent: Jan. 15, 1985

[54] DEVICE FOR OPENING AND CLOSING A CHUCK FOR A DENTAL HANDPIECE

[75] Inventor: Takasuke Nakanishi, Kanuma, Japan

[73] Assignee: Nakanishi Dental Mfg., Co., Ltd., Kanuma, Japan

[21] Appl. No.: 509,809

[22] Filed: Jun. 30, 1983

[30] Foreign Application Priority Data

Jul. 2, 1982 [JP] Japan .............................. 57-101183

[51] Int. Cl.³ ............................................... A61C 1/14
[52] U.S. Cl. .................................... 433/127; 433/129
[58] Field of Search ................... 279/75, 72, 71, 74, 279/30, 1 B; 433/129, 128, 126, 127

[56] References Cited

U.S. PATENT DOCUMENTS

| | | | |
|---|---|---|---|
| 2,010,210 | 8/1935 | Witt | 279/75 |
| 3,674,281 | 7/1972 | Hedrick | 279/1 B |
| 3,967,380 | 7/1976 | Maita et al. | 433/128 |

FOREIGN PATENT DOCUMENTS 1072069  11/1954  France .............................. 433/128

Primary Examiner—Robert Peshock
Attorney, Agent, or Firm—Wenderoth, Lind & Ponack

[57] ABSTRACT

A device for opening and closing a chuck for a dental handpiece has a handle portion and a powerhead assembly including a hollow driving shaft having, adjacent to its front end, a fowardly outwardly tapering portion joining a small diameter rear portion and a large diameter front portion. A hollow cylindrical chuck has a forwardly outwardly tapering outer peripheral surface joining a small diameter rear surface and a large diameter front surface corresponding to the respective driving shaft portions. The chuck is slidably inserted into the driving shaft. Three radial openings are formed at equally spaced positions in the forwardly outwardly tapering outer peripheral surface of the cylindrical chuck. A disc-shaped chucking die is slidably fitted into each radial opening to hold a dental tool. A chuck pusher is held in a socket with a disc plate spring interposed between the socket and the chuck pusher, and the pusher is movable for axially displacing the chuck to hold or release the dental tool.

7 Claims, 9 Drawing Figures

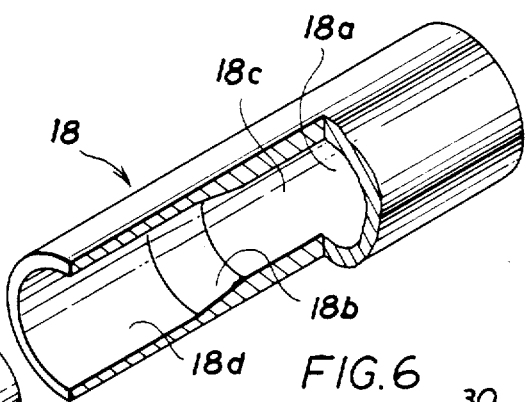
FIG. 5
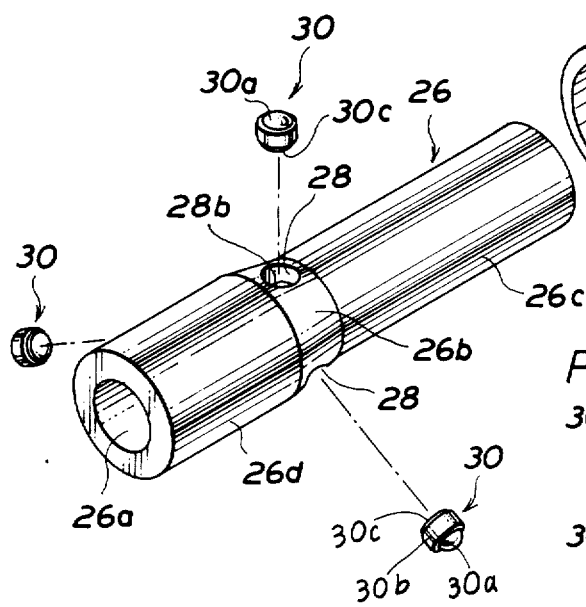
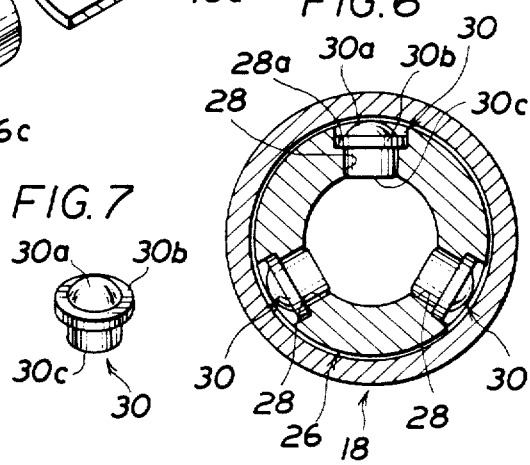
FIG. 6
FIG. 7
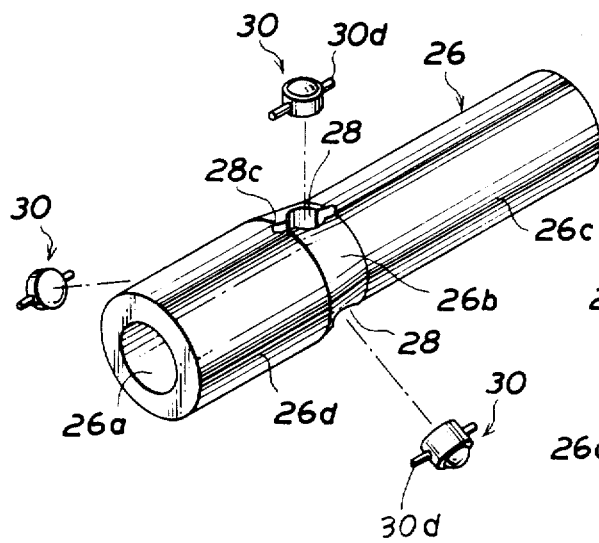
FIG. 8
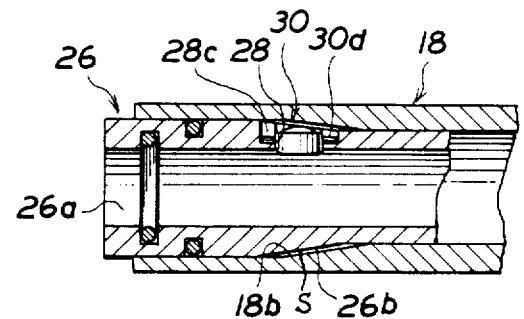
FIG. 9

DEVICE FOR OPENING AND CLOSING A CHUCK FOR A DENTAL HANDPIECE

BACKGROUND OF THE INVENTION

This invention relates to improvements in a chuck for a dental handpiece, and more particularly to a device for opening and closing a chuck for a dental handpiece which enables a dentist to exchange a dental tool easily.

In a conventional dental handpiece, a cylindrical pusher for a plurality of longitudinal slots is always pushed forward against the tapered inner periphery of the chuck so as to hold a dental tool firmly due to the flexibility of the chuck. However, this requires a special tool to displace the cylindrical pusher slidably. The exchanging operation of the dental tool using such a special tool is very troublesome for the dentist.

OBJECTS OF THE INVENTION

A principal object of this invention is to provide a device for closing and opening a chuck in a dental handpiece whereby dental tools such as drills, buffers, reamers, or the like can be easily and quickly chucked or released from the chuck of the dental handpiece.

Another object of this invention is to provide a device for closing and opening a chuck in a dental handpiece whereby the dental tools can be easily chucked, held firmly or released from the chuck by merely pressing a chuck pusher with a finger tip.

A further object of this invention is to provide a device which will enable the dentist to exchange a dental tool in a dental handpiece for a new one in a simpler and fast method and with ease of operation.

Still another object of this invention is to provide a device suitable for the aforementioned purposes which is small and comparatively simple in construction and at the same time rigid, strong and durable.

BRIEF DESCRIPTION OF DRAWINGS

While I have shown in the accompanying drawings a preferred embodiment of my invention, it should be understood that the same is susceptible of modification and change without departing from the spirit of my invention.

Referring to the drawings.

FIG. 5 is an exploded perspective view of the dental handpiece shown in FIGS. 1 and 2, with the chuck removed from the driving shaft and the driving shaft being partially cut away;

FIG. 6 is a section of another embodiment of the dental handpiece, similarly taken along the lines of IV—IV of FIG. 2;

FIG. 7 is a perspective view of a chucking die for insertion into a radial opening of the chuck;

FIG. 8 is a perspective view of still another embodiment of the dental handpiece shown in FIGS. 1 and 2, with its chucking die removed; and FIG. 9 is a fragmentary enlarged vertical sectional view of the dental handpiece shown in FIG. 8.

Referring to FIGS. 1 and 5, a preferred embodiment which has been selected to illustrate the present invention comprises a dental handpiece 10 including a handle portion 12 and a powerhead assembly 14 which is integrally connected to the handle portion 12 with the axis thereof perpendicular to the axis of handle portion 12.

Figure 1:
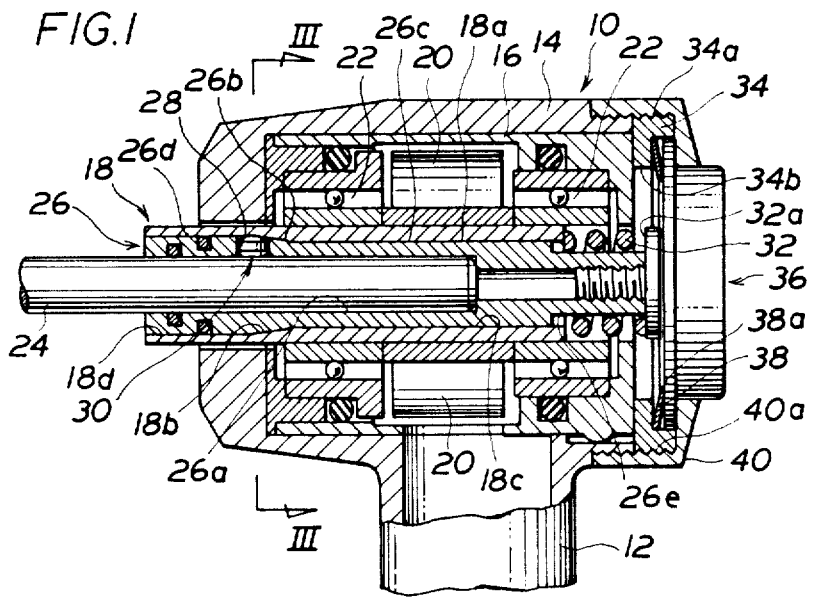
FIG. 1 is a fragmentary enlarged vertical sectional view of an embodiment of a dental handpiece according to this invention, with a dental tool inserted.

Integrally inserted into the handle portion 12 of the dental handpiece 10 is a bearing retainer 16, in which a driving shaft 18 having an axially extending hollow interior 18a and a plurality of radial turbine blades 20 around its periphery is journalled only for rotation in bearings 22. As particularly shown in FIGS. 1, 2 and 5, the hollow interior of the driving shaft 18 has, adjacent to its outer end, a forwardly outwardly tapering portion 18b which separates a small diameter rear portion 18c and a large diameter front portion 18d.

At the lower end of the powerhead assembly 14 is a pneumatic motor (not shown) which operates, when energized, to rotate at high speed a dental tool, the shank of which is shown at 24.

A cylindrical chuck 26 having an axially extending hollow interior 26a, a forwardly outwardly tapering outer peripheral surface 26b, a small diameter rear peripheral surface 26c, and a large diameter front peripheral surface 26d, corresponding to the forwardly outwardly tapering portion 18b, the small diameter rear portion 18c, and the large diameter front portion 18d respectively, is slidably inserted into the hollow interior 18a of the driving shaft 18.

Three radial openings 28 are provided at equally spaced positions around the outwardly tapering peripheral surface 26b of the cylindrical chuck 26.

A disc-shaped chucking die 30 having a diameter fitting into the radial opening 28 and a peripherally stepped flat bottom portion 30c is slidably inserted into the radial openings 28 of the cylindrical chuck 26 and projects slightly into the hollow interior 26a thereof, thus locating the disc-shaped chucking dies 30 at the outwardly tapering outer portion 18b of the driving shaft 18.

At the inner end of the cylindrical chuck 26 is a smaller diameter portion 26e, around which a helical compression spring 32 is wound. The rear end of the helical spring 32 bears against a spring seat 32a and its front end bears against the rear end of the driving shaft 18, thus always urging the cylindrical chuck 26 rearward.

A socket member 35 with a socket therein and having external peripheral threads 34a and a large central opening 34b is provided in an end portion of the bearing retainer 16.

A chuck pusher 36 is held in the socket of socket member 34 by a disc plate spring 38 interposed between the inner portion of the socket 34 and the chuck pusher 36, thus always urging the chuck pusher 36 rearward. A large opening 38a is formed at the central portion of the disc plate spring 38. A cap 40 having an internal peripheral threads 40a is screwed onto external threads 14a of the powerhead assembly 14 and the external peripheral threads 34a of the socket member 34. The pusher 36 in its normal rest position does not engage the rear end of chuck 26.

In FIGS. 6 and 7, another embodiment of the disc-shaped chucking die 30 is shown, in which a peripherally stepped recess 28a is formed around the radial opening 28 of the cylindrical chuck 26, and a peripheral seat flange 28b is provided around the bottom portion of the radial opening 28. A disc-shaped chucking die 30 having a diameter fitting into the radial opening 28, an umbrella-shaped head 30a, a peripheral flange 30b and a peripherally stepped flat bottom 30c is snugly fitting in position into the radial opening 28 of the cylindrical chuck 26 with the flat bottom 30c projecting slightly into the hollow interior 26a of the cylindrical chuck 26.

Figure 2:
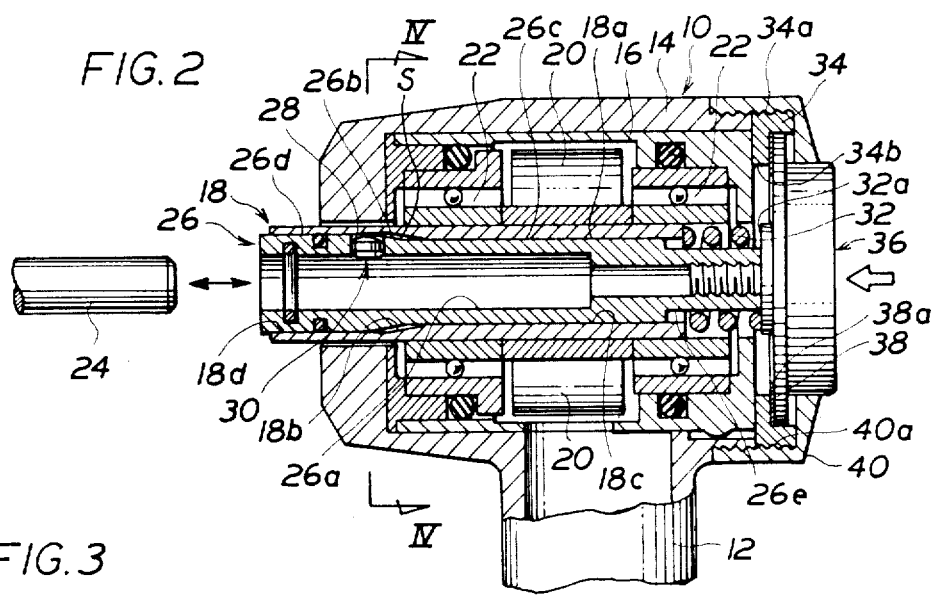
FIG. 2 is a similar enlarged vertical sectional view of the dental handpiece, with the dental tool released therefrom.
Figure 3:
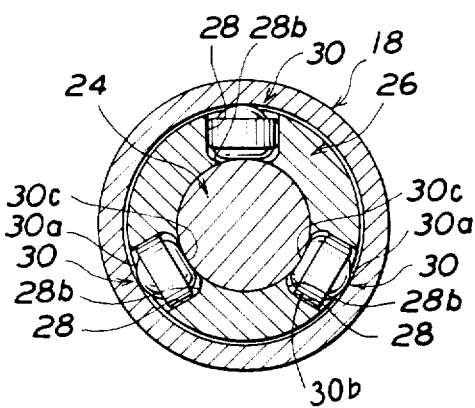
FIG. 3 is a section along the line III—III of FIG. 4.
Figure 4:
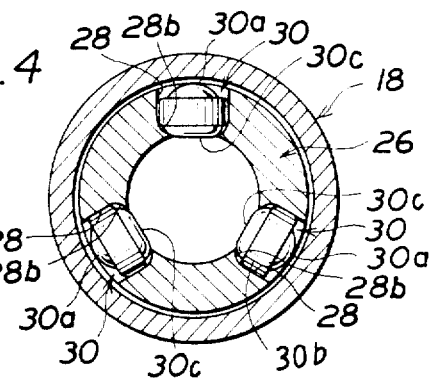
FIG. 4 is a section along the line IV—IV of FIG. 1.

FIG. 8 is a perspective view of another embodiment of the dental handpiece shown in FIGS. 1 and 2, wherein a pair of slot-shaped recesses 28c are provided diametrically opposite each other relative to radial opening 28 and extending longitudinally from the radially outer portion of the radial opening 28, and the disc-shaped chucking die 30 has a pair of diametrically extending legs 30d snugly received in the recesses 28c. FIG. 9 shows that when the disc-shaped chucking die 30 is snugly received in the radial opening 28 the supporting legs 30d are bottomed in the slots 28b thereof. Accordingly, the chucking die 30 can be oriented for sliding radially in opening 28 relative to the center of the cylindrical chuck 26.

For chucking the dental tool 24 into the dental handpiece 10, the chuck pusher 26 is pushed forwardly by a finger tip as shown by the arrow in FIG. 2 so as to compress the helical compression spring 32 and to move the cylindrical chuck 26 forwardly, thus forming a space S between the outwardly tapering portion 18a of the driving shaft 18 and the outwardly tapering outer peripheral surface 26a of the chuck 26, into which space the disc-shaped die 30 can shift radially.

In this situation, the dental tool 24 is inserted by fingers into the hollow interior 26a of the cylindrical chuck 26, and the disc-shaped die 30 which has the peripherally stepped flat bottom portion 30c projecting into the axially hollow portion 18a is forced to shift radially toward the outer periphery of the driving shaft 18 and to project its umbrella-shaped head portion 30a into the space S.

When the chuck pusher 36 is released, the chuck 26 is displaced axially rearwardly by the pulling force of the helical compression spring 32 to narrow the space S, to firmly interpose the disc-shaped die 30 between the forward outwardly tapering portion 18a and the outer periphery of the dental tool 24, to thereby chuck the l  r into the chuck 26 as shown in FIG. I.

When it is desired to disengage the dental tool 24 from the driving shaft 18 after operation, the chuck pusher 36 is again pushed forwardly to displace the chuck 26 forwardly, forming the space S as during chucking, allowing the chucking die 30 outwardly into the space S and also enabling the dentist to pull the dental tool 24 out of the chuck quite easily.

While the invention has been described in its preferred embodiments, it is to be understood that the words which have been used are words of description rather than of limitation and that changes within the purview of the appended claims may be made without departure from the true scope and spirit of the invention in its broader aspects.

I claim:

1. A dental handpiece having means for opening and closing a chuck, comprising:
    a handle portion;
    a powerhead assembly supported on said handle portion;
    a hollow driving shaft having a plurality of radial turbine blades around the periphery thereof and journalled only for rotation in said handle portion, said driving shaft having adjacent a forward end a large diameter front portion and a small diameter rear portion and a forwardly outwardly tapering portion joining said front and rear portions;
    a hollow cylindrical chuck axially slidably positioned in said hollow driving shaft, said cylindrical chuck having a large diameter front peripheral surface and a small diameter rear peripheral surface and a forwardly outwardly tapering outer peripheral surface joining said front and rear peripheral surfaces, said surfaces corresponding to said large diameter front portion, said small diameter rear portion and said forwardly outwardly tapering portion, respectively, said cylindrical chuck having a plurality of radial openings opening through said forwardly outwardly tapering surface at equally spaced positions therearound;
    a disc-shaped chucking die slidably positioned in each said radial opening and having a peripherally stepped flat bottom portion projecting slightly into the interior of said cylindrical chuck;
    a helical compression spring around said cylindrical chuck and having one end engaged with a rear portion of said cylindrical chuck and the other end engaged with a rearwardly facing surface of said driving shaft for urging said cylindrical chuck rearwards; and
    a chuck pusher in said powerhead assembly at the rear end of said cylindrical chuck and normally disengaged from said cylindrical chuck and engageable with said cylindrical chuck for sliding said cylindrical chuck within said driving shaft against said helical spring to release said chucking dies.

2. A dental handpiece as claimed in claim 1 in which the rear end of said powerhead assembly has a socket therein, said chuck pusher being slidable in said socket, and a circular plate spring in said socket for urging said chuck pusher rearwardly out of said socket, said plate spring having a large opening at the central portion thereof for allowing axial displacement of the rear end of said cylindrical chuck.

3. A dental handpiece as claimed in claim 1 wherein each said chucking die has a diameter for fitting into the corresponding radial opening and said peripherally stepped flat bottom portion is snugly engageable with the cylindrical shank of a dental tool for securely holding the dental tool in the cylindrical chuck.

4. A dental handpiece as claimed in claim 1 wherein said chucking die has an umbrella-shaped head, and said peripherally stepped flat bottom portion is snugly engageable with the cylindrical shank of a dental tool for securely holding the dental tool in the cylindrical chuck.

5. A dental handpiece as claimed in claim 1 wherein each chucking die has a pair of diametrically extending supporting legs, and said chuck has a pair of slits extending diametrically and longitudinally of said chuck from the outer portion of each radial opening for receiving said supporting legs.

6. A dental handpiece as claimed in claim 1 further comprising a socket member having said socket therein and fitted on the rear end of said powerhead assembly, and a cap threaded onto the external surface of said powerhead assembly and said socket member.

7. A dental handpiece as claimed in claim 6 wherein the rear end of said chuck has a spring seat thereon against which the rear end of said helical compression spring abuts.

* * * * *